United States Patent
Santarpia, III et al.

(10) Patent No.: US 6,770,266 B2
(45) Date of Patent: Aug. 3, 2004

(54) LIQUID TOOTH WHITENING COMPOSITION

(75) Inventors: R. Peter Santarpia, III, Edison, NJ (US); Michael Collins, Hazlet, NJ (US); John P. Curtis, Alpha, NJ (US); Richard S. Robinson, Hillsborough, NJ (US)

(73) Assignee: Colgate Palmolive Company, New York, NY (US)

( * ) Notice: Subject to any disclaimer, the term of this patent is extended or adjusted under 35 U.S.C. 154(b) by 42 days.

(21) Appl. No.: 10/155,496

(22) Filed: May 24, 2002

(65) Prior Publication Data

US 2003/0219390 A1 Nov. 27, 2003

(51) Int. Cl.[7] .................................. A61K 7/20
(52) U.S. Cl. .................. 424/53; 433/215; 433/216; 433/228.1
(58) Field of Search .................. 424/53; 433/215, 433/216

(56) References Cited

U.S. PATENT DOCUMENTS

| | | | | |
|---|---|---|---|---|
| 4,895,721 A | | 1/1990 | Drucker | 424/53 |
| 5,171,564 A | * | 12/1992 | Nathoo et al. | 424/53 |
| 6,083,421 A | * | 7/2000 | Huang et al. | 424/53 |
| 6,221,341 B1 | | 4/2001 | Montgomery | 424/53 |
| 6,306,370 B1 | | 10/2001 | Jensen et al. | 424/49 |
| 6,365,134 B1 | * | 4/2002 | Orlowski et al. | 424/53 |
| 6,419,905 B1 | * | 7/2002 | Alvarez | 424/53 |
| 6,419,906 B1 | * | 7/2002 | Xu et al. | 424/53 |
| 6,447,757 B1 | * | 9/2002 | Orlowski et al. | 424/45 |
| 6,485,709 B2 | * | 11/2002 | Banerjee et al. | 424/53 |
| 6,488,913 B2 | * | 12/2002 | Orlowski et al. | 424/53 |
| 6,503,486 B2 | * | 1/2003 | Xu et al. | 424/53 |
| 6,509,007 B2 | * | 1/2003 | Rajaiah et al. | 424/53 |
| 6,514,483 B2 | * | 2/2003 | Xu et al. | 424/53 |
| 6,517,350 B2 | * | 2/2003 | Diasti et al. | 433/215 |
| 6,569,408 B1 | * | 5/2003 | Yue et al. | 424/53 |

OTHER PUBLICATIONS

Colgate *Simply White* Trademark application 78121948 Dentifrice Toothpaste Bleaching Preparation, Apr. 16, 2002.*

Colgate *Simply White* Trademark application 75983041 Tooth Whitening Toothpaste, Jan. 20, 1999.*

Brian Wilk *Simply White* Tooth Whitening Dental Bleach Trademark application 75624163, Jan. 20, 1999.*

New Colgate Simply White Night Clear Whitening Gel w.w.w..colgatesimplywhite.com, Jul. 2003.*

\* cited by examiner

*Primary Examiner*—Shep K. Rose
(74) *Attorney, Agent, or Firm*—Bernard Lieberman

(57) ABSTRACT

An aqueous tooth whitening liquid composition comprising an orally acceptable vehicle comprising water and monohydric alcohol having dispersed therein a film forming combination of a poly(ethylene oxide) and a Carbomer, the pH of the composition being adjusted to and maintained at, an acid value.

5 Claims, No Drawings

LIQUID TOOTH WHITENING COMPOSITION

BACKGROUND OF THE INVENTION

1. Field of the Invention

This invention relates in general to tooth whitening liquids and more particularly to a stable, aqueous peroxide containing liquid whitening product useful for whitening tooth enamel.

2. The Prior Art

It has become desirable for a person's teeth to appear bright or "white". Society places a high value on the "whiteness" of one's teeth. One whose teeth are white may enjoy more personal confidence and satisfaction and may even enjoy greater social acceptance.

A tooth is comprised of an inner dentin layer and an outer hard enamel layer that is the protective layer of the tooth. The enamel layer of a tooth is naturally an opaque white or slightly off-white color. It is the enamel layer that can become stained or discolored. The enamel layer of a tooth is composed of hydroxyapatite mineral crystals that create a somewhat porous surface. These hydroxyapatite crystals form microscopic hexagonal rods or prisms that make up the enamel surface. As a result, the surface of the enamel layer presents microscopic spaces or pores between the prisms. It is believed that this porous nature of the enamel layer is what allows staining agents and discoloring substances to permeate the enamel and discolor the tooth. These remaining substances can occupy the microscopic spaces and eventually alter the color of the tooth.

Many substances that a person confronts or comes in contact with on a daily basis can "stain" or reduce the "whiteness" of one's teeth. In particular, the foods, tobacco products and fluids that one consumes tend to stain one's teeth. These products or substances tend to accumulate on the enamel layer of the tooth and form a pellicle film over the teeth. These staining and discoloring substances can then permeate the enamel layer. This problem occurs gradually over many years, but imparts a noticeable discoloration of the enamel of one's teeth. So long as the discolored teeth are still healthy and do not pose any health risk or problem, a product or substance that would whiten the discolored teeth would be advantageous.

It is also essential that a tooth whitening product that is to be used at home or in private by the consumer be safe and easy to use and be stable and retain its whitening efficacy during its storage on retail store shelves as well as over the period of use by the consumer.

Products and substances that are presently available to whiten teeth include a variety of different ingredients, but the primary active ingredient is a peroxide agent formulated into a liquid, solution, paste or gel. These products upon storage lose their whitening efficacy over time. A further limitation of commonly used aqueous peroxide solutions, is their brief period of efficacy when applied to the teeth in the oral cavity. For example, saliva, contains high concentrations of the enzyme catalase, which on contact, rapidly decomposes the peroxide into gaseous oxygen and water and so that there is only transitory contact of the peroxide whitening agent with the teeth. In addition, the low viscosities of aqueous peroxide solutions do not allow the peroxide whitening agent to remain in contact with the teeth for as long as is necessary to effect substantive whitening because of the constant flushing effects of salivary secretions. This tendency toward rapid decomposition of peroxide and the rapid flushing away of the peroxide agent applied to the teeth has severely limited their application to, and utility for, whitening teeth. It would be highly desirable, therefore, to provide a stable peroxide whitening liquid having increased retention on teeth to effect substantive whitening.

SUMMARY OF THE INVENTION

In accordance with one aspect of this invention there is provided a liquid dental whitening composition containing a peroxide whitening constituent dispersed in an aqueous liquid vehicle in which is dispersed a film forming component, the liquid composition rapidly drying when applied to the tooth surfaces to form in situ a gel-like film containing the peroxide whitening agent.

In one embodiment with the practice of the present invention, there is provided an aqueous tooth whitening liquid having enhanced stability and whitening efficacy, the liquid being comprised of an aqueous vehicle containing a film forming combination of an ethylene oxide linear homopolymer, a Carbomer and a peroxide whitening agent, the pH of the composition being maintained at an acidic level.

The aqueous liquid of the present invention is a portable oral care tooth whitener that can be conveniently painted onto the tooth surface. Upon the paint-on application to the teeth, the applied liquid whitening composition rapidly dries to produce, in situ, an adherent film of a thick liquid gel that has the capacity to release the peroxide whitening agent over an extended period of time. The film adheres to the tooth surface whereby the released peroxide source then whitens the teeth to which the film is applied, the film being sufficiently adherent to counteract the tooth flushing action of saliva generated in the oral cavity. The adjustment and maintenance of the composition pH to acid levels provides a peroxide source that is stable to decomposition on storage.

DESCRIPTION OF THE PREFERRED EMBODIMENTS

The vehicle used to prepare the liquid whitening composition of the present invention includes a non-toxic volatile monohydric alcohol or any suitable mixture thereof. The presence of the volatile monohydric alcohol imparts a rapid drying property to the applied liquid whitening composition and is present in the composition at a concentration of about 10 to about 50% by weight and preferably about 25 to about 40% by weight. Water is included in the vehicle of the composition and about 15 to about 35% by weight of the composition and preferably about 20 to about 30% by weight.

The proportion of vehicle used to prepare the liquid composition of the present invention is generally within the range of about 40 to about 80% by weight of the invention and preferably about 50 to about 70% by weight of the composition. A humectant such as sorbitol, glycerin or propylene glycol is present in the vehicle of the present invention at a concentration of about 2 to about 15% by weight and preferably about 3 to about 8 by weight.

Examples of poly(ethylene oxides) useful in the practice of the present invention include PEG 2M, 5M, 7M, 14M, 23M, 45M and 90M commercially available from Union Carbide, Danbury, Conn, ranging in molecular weight from 100,000 to 4 million. A poly(ethylene oxide) preferred for use in the practice of the present invention is a poly(ethylene oxide) having a molecular weight of about 100,000. Such poly(ethylene oxide) or PEG 2M is a nonionic polymer of ethylene oxide having an average molecular weight of 100,000 and has the general formula:

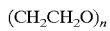

wherein n represents the number of repeating CH2CH2O groups.

Carbomers useful in the practice of the present invention include carboxymethylene polymers such as acrylic acid polymers, and acrylic acid copolymers. Carboxypolymethylene is a slightly acidic vinyl polymer with active carboxyl groups. A carboxypolymethylene preferred for use in the practice of the present invention is a water dispersible copolymer of acrylic acid cross-linked with approximately 0.75% to approximately 1.5% polyallyl sucrose that is sold under the trade designation Carbopol 934, 974 by B. F. Goodrich. The Carbopol product is present in the liquid whitening composition of the present invention at a concentration of about 0.25 to about 1.5% by weight and preferably about 0.5 to about 1.0% by weight.

Peroxide compounds which may be used as whitening agents in the practice of the present invention include hydrogen peroxide, urea peroxide and percarbonate salts such as sodium percarbonate. Most preferred is urea peroxide. The peroxide constituent is present in the liquid whitening compositions of the present invention at a concentration of about 5 to about 30% by weight and preferably about 10 to about 25% by weight.

At the acid pH levels at which the composition of the present invention is maintained the Carbomer of the Carbopol type behaves like a liquid gel rather than a solid gel so that the Carbomer in combination with the poly(ethylene oxide) constituent provides thickness to the liquid product while maintaining a consistency enabling the product to be painted on the tooth surface with a soft applicator brush.

The liquid whitening composition of the present invention may also contain a flavoring agent. Flavoring agents that are used in the practice of the present invention include essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint, spearmint and wintergreen. The flavoring agent is incorporated in the whitening liquid composition of the present invention at a concentration of about 0.1 to about 2% by weight and preferably about 0.1 to about 0.5% by weight.

The liquid whitening composition of the present invention is initially prepared in the form of a liquid varnish and applied as such to the users teeth as by painting the teeth with a soft applicator brush. After application by the user, the alcohol and water vehicle constituents rapidly evaporate to leave a film or coating of a thick liquid gel on the teeth to which the varnish has been applied. The deposited film is comprised of the poly(ethylene oxide) constituent, the Carbomer and constituent and the peroxide whitening agent or agents. The presence of the poly(ethylene oxide) and Carbomer constituent combination permits a slow release of the peroxide agent or agents to the applied tooth site, providing prolonged whitening treatment of the site.

The deposited film of liquid gel contains no ingredients imparting thereto an unacceptable taste or texture, rendering it unpleasant to the user and adheres strongly to tooth enamel. After application to the teeth, the composition dries in a relatively short time period, for example, 20 to 60 seconds to yield a strongly adherent, clear or tooth-colored film which is effectively invisible while in place. The film gel is sufficiently strong and adherent enough to remain on the teeth for a period of time, for example 10 to 30 minutes to effect a whitening result and will resist the forces commonly applied by the lips and tongue. While the film is in place, the user is to refrain from mastication. The film can be removed as and when required, at will, by an employment of standard oral hygiene procedures such as brushing or by rinsing with an alcoholic mouthwash. While in place the film releases agents contained therein at a slow, relatively constant rate and in concentration sufficient effectively to effect stain removal from the teeth.

The aqueous liquid whitening compositions of the present invention are prepared by adding and mixing the ingredients of the composition in a suitable vessel such as a stainless steel tank provided with a mixer. In the preparation of the liquid whitening composition, the ingredients are advantageously added to the mixer in the following order: water, Carbomer, alcohol, humectant, poly(ethylene oxide), and peroxide compound and any desired flavoring. The ingredients are then mixed to form a homogeneous dispersion/solution. To optimize the stability of the peroxide constituent present in the liquid whitening composition, the pH of the composition is adjusted to a pH of between about 3.5 and about 5.5 and preferably about 4.0 to about 4.5 with an orally acceptable acid such as phosphoric acid, lactic acid and malic acid or mixtures thereof which is generally added to the whitening liquid at a concentration of 0.05 to 2% by weight and preferably about 0.1 to about 1% by weight. The pH is buffered with a buffering agent such as sodium phosphate and sodium citrate and to maintain the acid value pH selected for the preparation of the liquid whitening composition.

The present invention is illustrated by the following example but is not to be limited thereby.

EXAMPLE

A whitening liquid having a pH of 4.0 was prepared having the following ingredients:

| Ingredient | % by Weight |
| --- | --- |
| Purified water | 25.1 |
| Carbopol 974 | 1.00 |
| 95% Ethyl alcohol | 34.8 |
| Glycerin | 5.00 |
| PEG 2M | 15.00 |
| Urea peroxide | 18.00 |
| 85% Phosphoric acid | 0.10 |
| Monobasic sodium phosphate | 1.0 |
| Total | 100.00 |

The shelf stability of the whitening liquid packaged in plastic bottles was determined by the percent urea peroxide recovered from the whitening liquid after a 4 to 12 week exposure to temperatures of 77° F. and 105° F. Peroxide recovery analysis was performed using Iodometric Titration. The stability results are recorded in Table I below.

TABLE I

LIQUID COMPOSITION STABILITY

| Elapsed Time | Initial Wt. % Peroxide | % Peroxide Recovery 77° F. | 105° F. | % Recovery of Peroxide |
|---|---|---|---|---|
| Initial | 18.4% | — | 18.4% | |
| 4 weeks | 18.7% | 100% | 17.3% | 94% |
| 8 weeks | 18.9% | 100% | 14.3% | 78% |
| 12 weeks | 18.7% | 100% | 8.4% | 46% |

The peroxide recovery results recorded in Table I indicate that the whitening liquid of the present invention retained sufficient peroxide content to be an efficacious whitening agent even after 12 weeks of storage at the elevated temperature of 105° F.

To determine the whitening efficacy of the liquid whitening composition of the Example, human studies were conducted. The evaluation procedure of the studies is described below.

In a first study, ninety (90) subjects participated and were randomly assigned to one of two groups and evaluated for extrinsic and intrinsic tooth staining. Twenty-nine subjects applied the liquid whitening composition of the Example to their front teeth twice a day for two weeks. Tooth examinations were performed on the first day and after the subject had used the product for two weeks. Upon examination each patients teeth were scored for extrinsic staining in which the stain adheres primarily to the tooth enamel surface. The extrinsic scoring was performed according to a modification of the Lobene Extrinsic Tooth Stain Index (R. R. Lobene, J. Am. Dent. Assoc. 77:849–855 (1968), in which the teeth are evaluated for staining area and intensity. The overall sum multiplication of the area and intensity scores of each tooth, yielded the stain index score, indicating the stain level.

For purposes of comparison, the procedure was repeated except the subjects in the second group of the first study used a commercially available, cellulose polymer based, liquid peroxide whitening composition of the type disclosed in U.S. Pat. No. 5,425,953, designated Composition C1 or a commercially available whitening toothpaste designated Composition C2. The extrinsic stain results are recorded in Table II below.

Intrinsic staining that is, staining trapped inside the tooth enamel was measured as shade guide improvement using Vita Lumin™ Vacuum Farbskala Shade Guides, a product of Vita Zahnfabrik, of Badsackinger, Germany which has 16 shades. The intrinsic staining results are recorded in Table III below.

TABLE II

EXTRINSIC STAIN (LOBENE) INDEX SCORES

| Composition | Baseline | 2 Week | % Reduction |
|---|---|---|---|
| Example | 32.20 ± 13.83 | 21.82 ± 12.39 | 32.24% |
| C1 | 36.03 ± 15.96 | 26.69 ± 18.27 | 25.92% |
| C2 | 36.73 ± 13.23 | 28.38 ± 12.20 | 22.73% |

TABLE III

INTRINSIC (SHADE GUIDE) STAIN RESULTS

| Composition | Baseline | 2 Week | Shade Improvement |
|---|---|---|---|
| Example | 11.28 ± 2.15 | 7.98 ± 4.06 | 3.38 |
| C1 | 11.20 ± 2.13 | 9.41 ± 3.63 | 1.69 |
| C2 | 11.44 ± 2.07 | 8.09 ± 3.77 | 3.29 |

A second study in which 40 subjects divided into groups of 20 participated, the procedure used in the first study to measure intrinsic stain was repeated. The comparative composition was Composition C2, a commercially available whitening toothpaste. The teeth of all the subjects were professionally cleaned prior to initiation of the study. The study was conducted for a three week period. The results are recorded in Table IV below.

TABLE IV

INTRINSIC (SHADE GUIDE) STAIN RESULTS

| Composition | Baseline | 3 Week | Shade Improvement |
|---|---|---|---|
| Example | 10.50 ± 1.90 | 6.28 ± 2.36 | 4.22 |
| C2 | 10.64 ± 2.00 | 10.31 ± 1.87 | 0.33 |

The results recorded in Tables II, III and IV demonstrate that the liquid whitening composition of the present invention is significantly more effective in the removal of extrinsic and intrinsic tooth stain when compared to a commercially available liquid whitening composition as well as a commercially available tooth whitening toothpaste.

What is claimed is:

1. An aqueous tooth whitening liquid composition suitable for application to teeth in the oral cavity comprising a peroxide dispersed in an orally acceptable vehicle comprising water and a monohydric alcohol and a film forming combination of a poly(ethylene oxide) and a Carbomer, wherein said film-forming poly(ethylene oxide) has a molecular weight from about 100,000 to 4,000,000, and is present in the composition in an amount from about 5 to about 50 weight %, and wherein the carbomer is a cross-linked acrylic acid copolymer and is present in an amount from about 0.25 to about 1.5 weight %, and wherein the peroxide is hydrogen peroxide, urea peroxide, or sodium percarbonate, and is present at a concentration of about 5 to about 30% by weight, wherein said monohydric alcohol is present at a concentration of about 10 to about 50% by weight, and thereby imparts a rapid drying property, and wherein water is included in a concentration of about 15 to about 70% by weight, and wherein said aqueous tooth whitening liquid composition has a PH maintained at about 3.5 to about 5.5 with a buffering salt, said carbomer at said acidic PH levels, in combination with said poly(ethylene oxide) maintaining a consistency enabling the product to be painted on the tooth surface, drying to yield a strongly adherent clear, or tooth-colored, invisible film, sufficiently strong and adherent to effect stain removal from the teeth as a whitening result.

2. The composition of claim 1 wherein a humectant is present in the vehicle humectant.

3. The composition of claim 2 wherein humectant is present in an amount from about 3.0 weight % to about 8.0 weight %.

4. The composition of claim 1 wherein the aqueous vehicle is present in an amount from about 40 to about 70 wt. %.

5. A method for whitening teeth which comprises
(a) preparing a tooth whitening composition of claim 1;
(b) painting the composition into contact with the teeth to be whitened;
(c) maintaining the composition in contact with the teeth for plurality of minutes per day; and then,
(d) repeating steps b and c for multiple days to thereby whiten the teeth.

* * * * *